US00PP11757P2

(12) United States Plant Patent
VandenBerg

(10) Patent No.: US PP11,757 P2
(45) Date of Patent: Jan. 30, 2001

(54) CHRYSANTHEMUM PLANT NAMED 'YOABILENE'

(75) Inventor: Cornelis P. VandenBerg, Salinas, CA (US)

(73) Assignee: Yoder Brothers, Inc., Barberton, OH (US)

( * ) Notice: Under 35 U.S.C. 154(b), the term of this patent shall be extended for 0 days.

(21) Appl. No.: 09/270,790

(22) Filed: Mar. 17, 1999

(51) Int. Cl.[7] ..... A01H 5/00

(52) U.S. Cl. ..... Plt./290

(58) Field of Search ..... Plt./287, 290

(56) References Cited

U.S. PATENT DOCUMENTS

P.P. 6,801 * 5/1989 VandenBerg ..... Plt./290

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Yoabilene', characterized by its uniformly mounded plant habit; freely branching habit, very full and dense plants; dark green leaves; uniform flowering; decorative disbud-type inflorescences that are about 8.8 cm in diameter; attractive golden bronze-colored ray florets; and good postproduction longevity with inflorescences and leaves maintaining good substance and color for about three weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yoabilene.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in December, 1994, in Salinas, Calif., of a proprietary Chrysanthemum seedling selection identified as code number YB-4779 as the male, or pollen, parent, with the commercial Chrysanthemum cultivar Charm, disclosed in U.S. Plant Pat. No. 5,502, as the female, or seed, parent.

The new Chrysanthemum was discovered and selected by the Inventor as a flowering plant within the progeny of the stated cross in a controlled environment in Fort Myers, Fla., in November, 1995. The selection of this plant was based on its desirable inflorescence form and floret colors and good post-production longevity.

Asexual reproduction of the new Chrysanthemum by terminal cuttings harvested in a controlled environment in Fort Myers, Fla., has shown that the unique features of this new Chrysanthemum are stable and reproduced true to type in successive generations.

SUMMARY OF THE INVENTION

The cultivar Yoabilene has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yoabilene'. These characteristics in combination distinguish 'Yoabilene' as a new and distinct Chrysanthemum:

1. Uniformly mounded plant habit.
2. Freely branching habit, very full and dense plants.
3. Dark green leaves.
4. Uniform flowering.
5. Decorative disbud-type inflorescences that are about 8.8 cm in diameter.
6. Attractive golden bronze-colored ray florets.
7. Good postproduction longevity with inflorescences and leaves maintaining good substance and color for about three weeks in an interior environment.

The new Chrysanthemum can be compared to the Chrysanthemum cultivar Copper Charm, disclosed in U.S. Plant Pat. No. 9,913. However in side-by-side comparisons in Salinas, Calif., and Leamington, Ontario, Canada, under commercial practice, plants of the new Chrysanthemum differed from plants of the cultivar Copper Charm in the following characteristics:

1. Plants of the new Chrysanthemum are more compact than plants of the cultivar Copper Charm.
2. Plants of the new Chrysanthemum have darker green leaves than plants of the cultivar Copper Charm.
3. Inflorescences of plants of the new Chrysanthemum are smaller, but taller than inflorescences of plants of the cultivar Copper Charm.
4. Ray florets of plants of the new Chrysanthemum are shorter, wider and more reflexed than ray florets of plants of the cultivar Copper Charm.
5. Ray florets of plants of the new Chrysanthemum are golden bronze in color whereas ray florets of plants of the cultivar Copper Charm are copper bronze in color.
6. Plants of the new Chrysanthemum flower about one week later than plants of the cultivar Copper Charm.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a side perspective view of a typical flowering plant of 'Yoabilene'.

The photograph at the bottom of the first sheet comprises a close-up view of upper (left) and lower (right) surfaces of typical inflorescences and leaves of the cultivar Yoabilene.

The photograph at the top of the second sheet comprises a side perspective view of typical flowering plants of 'Yoabilene' (left) and 'Copper Charm' (right).

The photograph at the bottom of the second sheet comprises a close-up view of upper surfaces of typical inflorescences and leaves of plants of 'Yoabilene' (left) and 'Copper Charm' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yoabilene.

Commercial classification: Decorative disbud-type pot Chrysanthemum.

Parentage:

*Male or pollen parent.*—Proprietary *Dendranthema grandiflora* seedling selection identified as code number YB-4779.

*Female or seed parent.*—*Dendranthema grandiflora* cultivar Charm, disclosed in U.S. Plant Pat. No. 5,502.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative disbud-type pot Chrysanthemum. Inverted triangle; stems mostly upright and outwardly spreading giving a uniformly mounded appearance to the plant. Freely branching: about five lateral branches develop after removal of terminal apex (pinching); dense and full plants.

*Plant height.*—Medium, about 29 cm.

*Plant width.*—About 44 cm.

*Stem color.*—Close to 147A.

*Stem texture.*—Pubescent.

*Foliage description.*—Arrangement: Alternate. Length: About 8.1 cm. Width: About 5 cm. Apex: Mucronate. Base: Attenuate. Margin: Palmately lobed, sinuses between lateral lobes mostly parallel. Texture: Upper and lower surfaces with very fine pubescence; veins prominent on lower surface. Petiole length: About 2.1 cm. Color: Young foliage upper surface: Darker than 147A. Young foliage lower surface: Close to 147B. Mature foliage upper surface: 147A. Mature foliage lower surface: 147B. Venation upper surface: 147B. Venation lower surface: Close to 147B.

Inflorescence description:

*Appearance.*—Decorative disbud-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about nine weeks later.

*Postproduction longevity.*—Inflorescences and leaves will maintain good color and substance for about three weeks in an interior environment.

*Quantity of inflorescences.*—As a disbud-type, all lateral inflorescences are removed to allow for maximum terminal inflorescence size. One inflorescence per lateral stem; about five inflorescences per plant.

*Inflorescence bud.*—Height: About 6 mm. Diameter: About 9 mm. Color: Close to 147A.

*Inflorescence size.*—Diameter: About 8.8 cm. Depth (height): About 2.6 cm. Diameter of disc: About 8.5 mm, inconspicuous.

*Ray florets.*—Shape: Oblong with short corolla tube. Orientation: Initially upright, then concave and eventually reflexed when fully expanded. Length: About 4.2 cm. Width: About 1.5 cm. Apex: Mostly emarginate. Margin: Entire. Texture: Smooth, glabrous; longitudinally ridged. Number of ray florets per inflorescence: About 224. Color: When opening: Initially light yellow, close to 4B; becoming more bronze, closest to 163A, overlaid with 164A. Fully opened, upper surface: Close to 9A to 163A–163B overlaid with 164A; more yellow towards apex. When plants of the new Chrysanthemum are grown under cool production temperatures, ray florets may be darker and/or more orange in color. Fully opened, lower surface: Light yellow, closest to 8A, overlaid with 162A.

*Disc florets.*—Shape: Tubular. Apex: Serrated. Length: About 4 mm. Width: Apex: About 1 mm. Base: About 1 mm. Number of disc florets per inflorescence: Few, about 36. Color: Immature: Greener than 154A. Mature: Apex: 9A. Mid-section and base: White, 155D.

*Reproductive organs.*—Androecium: Present on disc florets only. Anther color: 13A. Pollen: Amount: Scarce. Color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yoabilene', as illustrated and described.

* * * * *

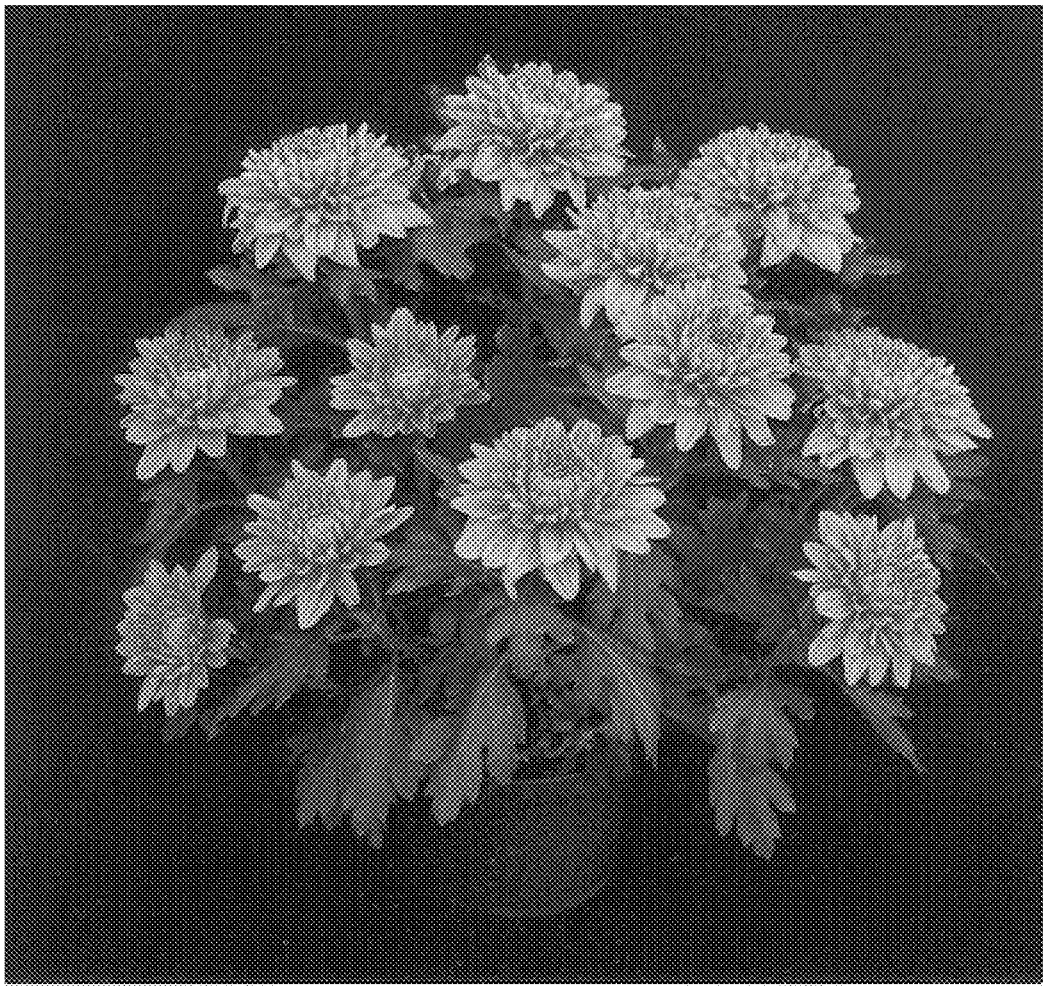
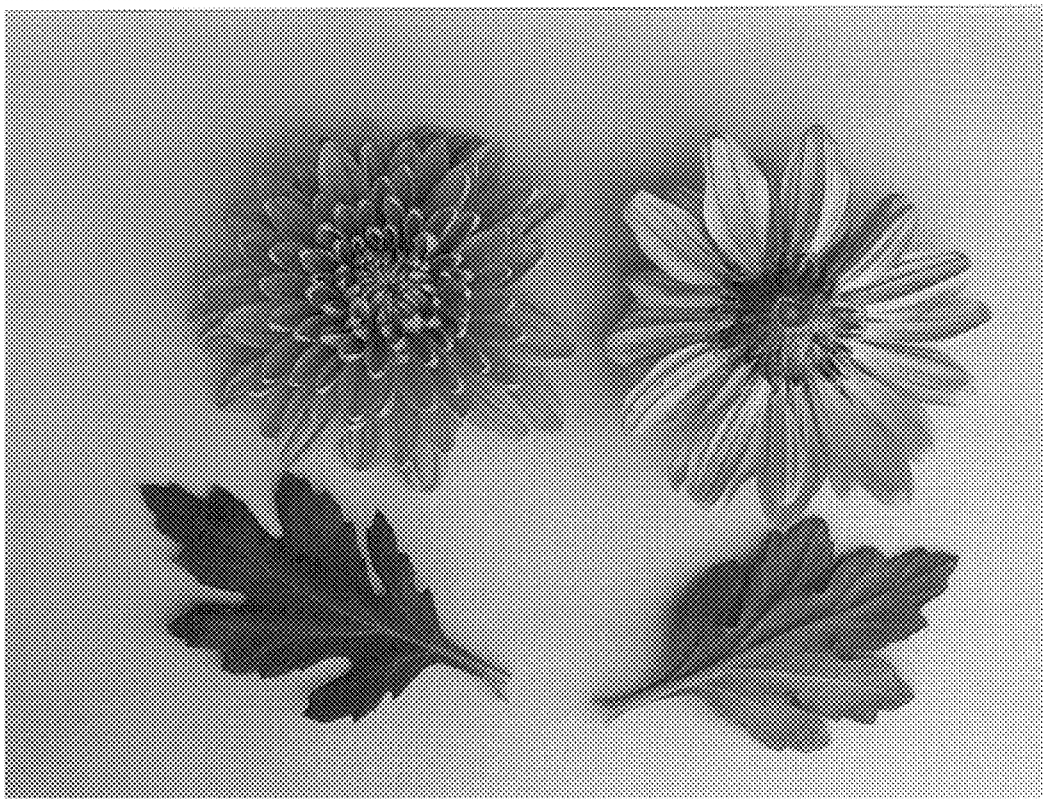

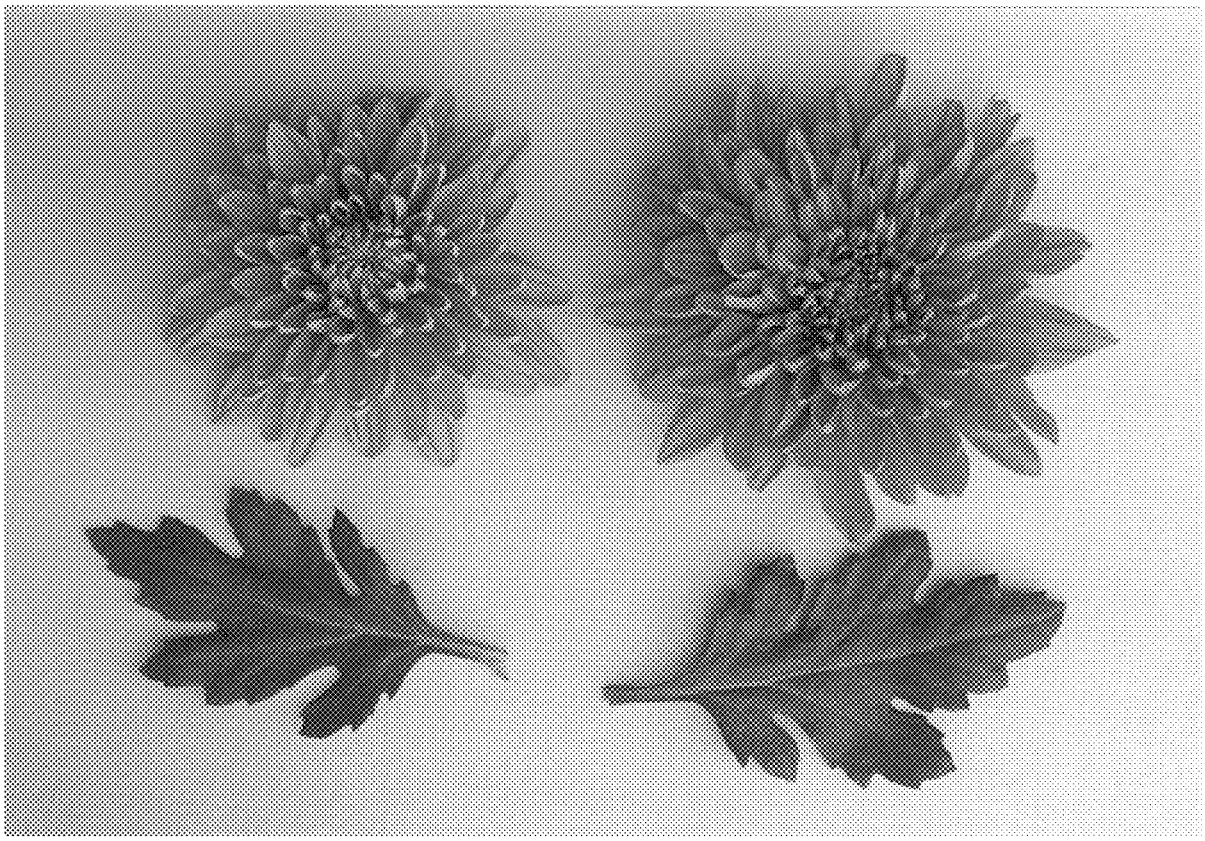

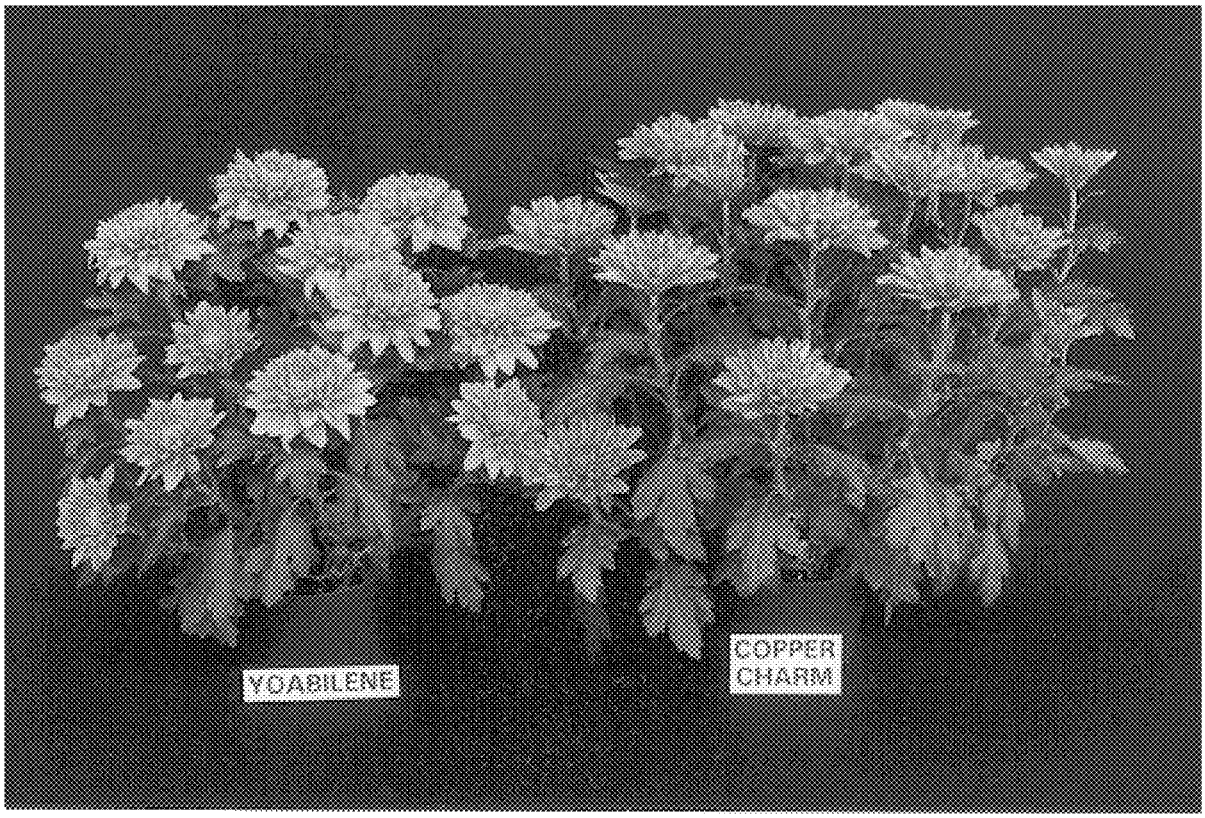
YOABILENE
COPPER
CHARM